US006312682B1

(12) United States Patent
Kingsman et al.

(10) Patent No.: US 6,312,682 B1
(45) Date of Patent: Nov. 6, 2001

(54) RETROVIRAL VECTORS

(75) Inventors: Alan John Kingsman; Susan Mary Kingsman, both of Oxon; Narry Kim; Kyriacos Mitrophanous, both of Oxford, all of (GB)

(73) Assignee: Oxford BioMedica plc, Oxford (GB)

( * ) Notice: Subject to any disclaimer, the term of this patent is extended or adjusted under 35 U.S.C. 154(b) by 0 days.

(21) Appl. No.: 09/224,014

(22) Filed: Dec. 28, 1998

Related U.S. Application Data

(63) Continuation of application No. PCT/GB97/02857, filed on Oct. 17, 1997.

(30) Foreign Application Priority Data

Oct. 17, 1996 (GB) .................................................. 9621680
Nov. 25, 1996 (GB) .................................................. 9624457

(51) Int. Cl.$^7$ ........................... A61K 48/00; C12N 15/88
(52) U.S. Cl. .................. 424/93.2; 435/91.4; 435/320.1; 435/325; 435/455; 514/44
(58) Field of Search ............................... 435/320.1, 455, 435/325, 91.4; 424/93.21, 93.2; 536/23.1; 514/44

(56) References Cited

U.S. PATENT DOCUMENTS 6,013,516    1/2000    Verma et al. ........................ 435/325

FOREIGN PATENT DOCUMENTS

| 0 611 822 A2 | 8/1994 | (EP) . |
|---|---|---|
| 0 759 471 A1 | 2/1997 | (EP) . |
| WO 91/19798 | 12/1991 | (WO) . |
| WO 92/21750 | 12/1992 | (WO) . |
| 97/14809 | 4/1997 | (WO) . |
| WO 97/12622 | 4/1997 | (WO) . |

OTHER PUBLICATIONS

Journal of Virology 97, 1997, p.6641–6649, Blömer et al., "Highly Efficient and Sustained Gene Transfer in Adult Neurons with a Lentivirus Vector".
Human Molecular Genetics 5, 1996, p. 1397–1404, Blömer et al., "Applications of gene therapy to the CNS".
Journal of Virology 69, 1995, p. 2101–2109, Clever et al., RNA Secondary Structure and Binding Sites for gag Gene Products in the 5′ Packaging Signal of Human Immundeficiency Virus Type 1.
Journal of Virology 71, 1997, p.3407–3414, Clever et al., "Mutant Human Immunodeficiency Virus Type 1 Genomes with Defects in RNA Dimerization or Encapsidation".
Fields of Virology 3, 1996, p. 1767–1996, John M. Coffin, "Retroviridae: The Virsuses and Their Replication".
Cell 38, 1984, p. 65–77, p. 65–77, Fuller et al., "Vesicular Stomatitis Virus Infects and Matures Only through the Basolateral Surface of the Polarized Epithelial Cell Line, MDCK".

Aids Research and Human Retroviruses 8, 1992, p. 39–45, Harrison et al., "Inhibition of HIV Production in Cells Containing an Integrated, HIV–Regulated Diphtheria Toxin A Chain Gene".
Virology 188, 1992, p. 590–599, Hayashi et al., "RNA Packaging Signal of Human Immunodeficiency Virus Type 1".
Journal of Virology 72, 1998, p. 811–816, Kim et al., "Minimal Requirement for a Lentivirus Vector Based on Human Immunodeficiency Virus Type 1".
Journal of Virology 63, 1989, p. 3708–3713, Kim et al., "Temporal Aspects of DNA and RNA Synthesis during Human Immunodeficiency Virus Infection: Evidence for Differential Gene Expression".
Cell, vol. 33, 1983, p. 153–159, Mann et al., "Construction of a Retrovirus Packaging Mutant and Its Use to Produce Helper Free Defective Retroviruses".
Journal of Virology 68, 1994, p. 3102–3111 Martarano et al., "Equine Infectious Anemia Virus trans–Regulatory Protein Rev Controls Viral mRNA Stability, Accumulation, and Alternative Splicing".
Journal of General Virology 75, 1994, p. 425–429, Payne et al., "Characterization of infectious molecular clones of equine infectious anaemia virus".
Proc. Natl. Acad. Sci. USA 91, 1994, p. 9564–9568, Yee et al., "A general method for the generation of high–titer, pantropic retroviral vectors: Highly efficient infection of primary hepatocytes".
BioTechniques 19, 1995, p. 352–354, Carroll et al., "*E. coli* beta–Glucuronidase (GUS) as a Marker for Recombinant Vaccinia Viruses".
Virology 238, 1997, p. 198–211, Carroll et al., "Host Range and Cytopathogenicity of the Highly Attenuated MVA Strain of Vaccinia Virus: Propagation and Generation of Recombinant Viruses in a Nonhuman Mammalian Cell Line".
Molecular and Cellular Biology, 5, 1985, p. 3403–3409, Chakrabarti et al., "Vaccinia Viruse expression Vector: Coexpression of beta–Galactosidase Provides Visual Screening of Recombinant Virus Plaques".
BioTechniques 23, 1997, p. 1094–1097, Chakrabarti et al., "Compact, Synthetic, Vaccinia Virus Early/Late Promoter for Protein Expression".
J. Mol. Biol. 210, 1989, p. 749–769, Davison et al., "Structure of Vaccinia Virus Early Promoters".
J. Mol. Biol. 210, 1980, p. 771–784, Davison et al. "Structure of Vaccinia Virus Late Promoters".

(List continued on next page.)

*Primary Examiner*—Dave T. Nguyen
(74) *Attorney, Agent, or Firm*—Frommer Lawrence & Haug; Thomas J. Kowalski

(57) ABSTRACT

Retroviral vector production systems for producing lentivirus-based vector particles which are capable of infecting and transducing non-dividing target cells, wherein one or more of the auxiliary genes such as vpr, vif, tat, and nef in the case of HIV-1 are absent from the system. The systems and resulting retrovirus vector particles have improved safety over existing systems and vectors.

71 Claims, 3 Drawing Sheets

OTHER PUBLICATIONS

Current Protocols in Molecular Biology 1998, Suppl. 43 Unit 16.16, Earl et al., "Preparation of Cell Cultures and Vaccinia Virus Stocks".

Current Protocols in Molecular Biology 1998, Suppl. 43 Unit 16.17, Earl et al., "Generation of Recombinant Vaccinia Viruses".

Nature 330, 1987, p 259–262, Flexner et al. "Prevention of vaccinia virus infection in immunodeficient mice by vector–directed IL–2 expression".

Journal of Virology 71, 1997, p. 4997–5002, Holzer et al., "Construction of a Vaccinia Virus Deficient in the Essential DNA Repair Enzyme Uracil DNA Glycosylase by a Complementing Cell Line".

Proc. Natl. Acad. Sci. USA 79, 1982, p. 7415–7419, Mackett et al., "Vaccinia virus: A selectable eukaryotic cloning and expression vector".

Berl. und Münchener Tierärtzliche Wochenschrift 107, 1994, p. 253–256, Mahnel et al., "Erfahrungen bei der Schutzimpfung gegen Orthopocken von Mensch und Tier mit dem Impstamm MVA", English translation.

Zentralbl. Bakteriol, 1978, p. 375–390, Mayr et al., "The Smallpox Vaccination Strain MVA: Marker, Genetic Structure, Experience Gained with the Parenteral Vaccination and Behavior in Organisms with a Debilitated Defence Mechansism" (English Abstract).

Journal of General Virology 72, 1991, p. 1031–1038, Meyer et al., "Mapping of deletions in the genome of the highly attenuated vaccinia virus MVA and their influence on virulence".

Fields Virology 3, 1996, p. 2637–2672, Bernard Moss, "Poxviridae: The Viruses and Their Replication".

Adv Exp Med Biol 367, 1996, p. 7–13, Moss et al., "Host Range Restricted Non–Replicating Vaccinia Virus Vectors as Vaccine Candidates".

Proc. Natl. Acad. Sci. USA, 79, 1982, p. 4927–4931, Panicali et al., "Construction of poxviruses as cloning vectors: Insertion of the thymidine kinase gene from herpes simplex virus into the DNA of infectious vaccinia virus".

Nucleic Acids Research, vol. 23, 1995, p. 628–633, Soneoka et al., "A transient three–plasmid expression system for the production of high titer retroviral vectors".

Proc. Natl. Acad. Sci. USA, 1992, p. 10847–10851, Sutter et al., "Nonreplicating vaccinia vector efficiently expresses recombinant genes".

Virology 187, 1992, p. 321–328, Taylor et al., "Nonreplicating Viral Vectors as Potential Vaccines: Recombinant Canarypox Virus Expressing Measles Virus Fusion (F) and Hemagglutinin (HA) Glycoproteins".

Dev Biol Stand 82, 1994, p 65–69, Paoletti et al., "Safe and Effective Poxvirus Vectors–NYVAC and ALVAC".

Virology 210, 1995, p 202–205, Wyatt et al., "Replication–Deficient Vaccinia Virus Encoding Bacteriophage T7 RNA Polymerase for Transient Gene Expression in Mammalian Cells".

Virology 251, 1998, p 334–342, Wyatt et al., "Marker Rescue of the Host Range Restriction Defects of Modified Vaccinia Virus Ankara".

Vaccine 14, 1996, p. 1451–1458, Wyatt et al., "Development of a replicaiton–deficient recombinant vaccinia virus vaccine effective against parainfluenza virus 3 infection in an animal model".

W. French Anderson. Human gene therapy. Nature. vol. 392, pp. 25–30, 1998.*

Verma et al. Gene therapy–promises, problems and prospects. Nature. vol. 389, pp. 239–242. 1997.*

Science, vol. 272, Apr. 12, 1996, pp. 263–267, L. Naldini et al., "In vivo Gene Delivery and Stable Transduction of Nondividing cells by a Lentiviral Vector", XP000583652.

Nature Biotechnology vol. 15, Sep. 1997, pp. 871–875, Zufferey et al., "Multiply attenuated lentiviral vector achieves efficient gene delivery in vivo", XP–002056816.

Journal of Virology, Apr. 1996, pp. 2581–2585, Akkina et al. "High–Efficiency Gene Transfer into CD34+ Cells with a Human Immunodeficiency Virus Type 1–Based Retroviral Vector Pseudotyped with Vesicular Stomatitis Virus Envelope Glycoprotein G".

Proc. Natl. Acad. Sci. USA, vol. 90, Sep. 1993, pp. 7941–7945, Barillari et al., "The Tat protein of human immunodeficiency virus type 1, a growth factor for AIDS *Kaposi sarcoma* and cytokine–activated vascular cells, induces adhesion of the same cell types by using integrin receptors recognizing the RGD amino sequence".

Journal of Virology, May 1992, pp. 2731–2739, Buchschacher, Jr. et al., "Human Immunodeficiency Virus Vectors for Inducible Expression of Foreign Genes".

Nature, vol. 365, Oct. 14, 1993, pp. 666–669, Bukrinsky et al., "A nuclear localization signal within HIV–1 matrix protein that governs infection of non–dividing cells".

Journal of Virology, Nov. 1996, pp. 8234–8240, Cannon et al., "Murine Leukemia Virus–Based Tat–Inducible Long Terminal Repeat Replacement Vectors: a New System for Anti–Human Immunodeficiency Virus Gene Therapy".

Molecular and Cellular Biology, Aug. 1987, p. 2745–2752, Chen et al., "High–Efficiency Transformation of Mammalian Cells by Plasmid DNA".

Journal of Acquired Immune Deficiency Syndromes, 1994 Raven Press, Ltd., New York, pp. 655–664, Echetebu et al., "Construction and Characterization of a Potent HIV–2 Tat Transdominant Mutant Protein".

Nature, vol. 345, May 3, 1990, pp. 84–87, Ensoli et al., "Tat protein of HIV–1 stimulates growth of cells derived from Kaposi's sarcoma lesions of AIDS patients".

Journal of Virology, Feb. 1996, pp. 1027–1032, Gallay et al., "Role of the Karyopherin Pathway in Human Immunodeficiency Virus Type 1 Nuclear Import".

Proc. Natl. Acad. Sci. USA, vol. 91, Jul. 1994, pp. 7311–7315, Heinzinger et al., "The Vpr protein of human immunodeficiency virus type 1 influences neclear localization of viral nucleic acids in nondividing host cells".

Fields Virology, Third Edition, 1996, chapter 62, pp. 1977–1996, Joag et al., "Lentiviruses".

Journal of Virology, Oct. 1995, pp. 6304–6313, Jowett et al., "The Human Immunodeficiency Virus Type 1 vpr Gene Arrestes Infected T Cells in the $G_2$ + M Phase of the Cell Cycle".

Journal of Virology, Sep. 1989, pp. 3708–3713, Sunyoung Kim et al., "Temporal Aspects of DNA and RNA Synthesis during Human Immunodeficiency Virus Infection: Evidence for Differential Gene Expression".

Journal of Virology, Sep. 1989, pp. 4085–4087, Lever et al., "Identification of a Sequence Required for Efficient Packaging of Human Immunodeficiency Virus Type 1 RNA into Virions".

Cell, vol. 72, Feb. 26, 1993 pp. 541–550, Levy et al., "Induction of Cell Differentiation by Human Immunodeficiency Virus 1 vpr".

Cell, vol. 72, Feb. 26, 1993 pp. 1245–1252.

Journal of Virology, vol. 69, Feb. 1995, pp. 1243–1252, Levy et al., "Extracellular Vpr Protein Increases Cellular Permissiveness to Human Immunodeficiency Virus Replication and Reactivates Virus from Latency".

Proc. Natl. Acad. Sci. USA, vol. 90, Sep. 1993, pp. 8000–8004, Lisziewicz et al., "Inhibition of human immunodeficiency virus type 1 replication by regulated expression of a polymeric Tat activation response RNA decoy as a strategy for gene therapy in AIDS".

Virology 212, 1995, pp. 331–339, Mahalingham et al., "Functional Analysis of HIV–1 Vpr: Identification of Determinants Essential for Subcellular Localization".

Science, vol. 272, Apr. 12, 1996, pp. 263–267, Naldini et al., "In Vivo Gene Delivery and Stable Transduction of Nondividing Cells by a Lentiviral Vector".

Proc. Natl. Acad. Sci. USA, vol. 93, Oct. 1996, pp. 11382–11388, Naldini et al., Efficient transfer, integration, and sustained long–term expression of the transgene in adult rat brains injected with a lentiviral vector.

Journal of Virology, vol. 64, No. 1, Nov. 1990, pp. 5270–5276, Page et al., "Construction and Use of a Human Immunodeficiency Virus Vectro for Analysis of Virus Infectivitiy".

Journal of Virology, vol. 65, No. 1, Jan. 1991, pp. 531–536, Poznansky et al., "Gene Transfer into Human Lymphocytes by a Defective Human Immunodeficiency Virus Type 1 Vector".

Journal of General Virology, vol. 76, 1995, pp. 691–696, Richardson et al., "Helper virus free transfer of human immunodeficiency virus type 1 vectors".

Human Gene Therapy 7, vol. 77, Sep. 10, 1996, pp. 1781–1790, Ross et al., "Gene Therapy in the United States: A Five–Year Status Report".

The Journal of Clinical Investigation, Inc., vol. 88, Sep. 1991, 1043–1047, Shimada et al., "Targeted and Highly Efficient Gene Transfer into CD4+ Cells by a Recombinant Human Immunodeficiency Virus Retroviral Vector".

Journal of General Virology, 1996, pp. 1611–1621, Tomonaga et al., "Molecular biology of the feline immunodeficiency virus auxiliary genes".

Journal of Virology, vol. 68, No. 1, Jan. 1994, pp. 510–516, Fred Hutchinson Cancer Research, "Passage through Mitosis Is Required for Oncoretroviruses but Not for the Human Immunodeficiency Virus".

Journal of Virology, vol. 66, No. 5, May 1992, pp. 2731–2739, Buchschacher et al., "Human Immunodeficiency Virus Vectors for Inducible Expression of Foreign Genes".

Science, vol. 272, Apr. 12, 1996, Naldini et al., "In Vivo Gene Delivery and Stable Transduchtion of Nondividing Cells by a Lentiviral Vector".

British Medical Bulletin, 1995, vol. 51, pp. 12–30, R G Vile et al., "Retroviruses as vectors".

Journal of Virology, Jul. 1988, pp. 2464–2473, Bowtell et al., "Comparison of Expression in Hemopoietic Cells by Retroviral Vectors Carrying Two Genes".

Blood, vol. 84, No. 6, Sep. 15, 1994, pp. 1812–1822, Correll et al., "Retroviral Vector Design for Long–Term Expression in Murine Hematopoietic Cells In Vivo".

Cell, vol. 39, Dec. 1984, pp. 458–467, Emerman et al., "Genes with Promoters in Retrovirus Vectors Can Be Independently Suppressed by an Epigenentic Mechanism".

Molecular and Cellular Biology, Dec. 1991, pp. 5848–5859, Ghattas et al., "The Encephalomyocarditis Virus Internal Ribosome Entry Site Allows Efficient Coexpression of Two Genes from a Recombinant Provirus in Cultered Cells and in Embryos".

Proc. Natl. Acad. Sci. USA, vol. 86, May 1989, pp. 3519–3523, Hantzopoulos et al., "Improved gene expression upon transfer of the adenosine deaminase minigene outside the transcriptional unit of a retroviral vector".

The Journal of Biological Chemistry, vol. 266, issue of May 5, 1991, pp. 6416–6425, Hatzoglou et al., "Hormonal Control of Interacting Promoters Introduced into Cells by Retroviruses".

The Journal of Biological Chemistry, vol. 268, No. 33, Nov. 26, 1988, pp. 17798–17808, Hatzoglou et al., "Hormonal Regulation of Chimeric Genes Containing the Phospphoenolpyruvate Carboxykinase Promoter Regulatory Region in Hepatoma Cells Infected by Murine Retroviruses".

Human Gene Therapy, 1992, pp. 381–390, Hantzopoulos et al., "Comparison of the Expression of a Mutant Dihydofolate Reductase under Control of Different Internal Promoters in Retroviral Vectors".

Virology 195, 1993, pp. 1–5, McLachlin et al., "Factors Affecting Retroviral Vector Function and Structural Integrity".

Molecular and Cellular Biology, Apr. 1988, pp. 1803–1808, Overall et al., "Stably Transmitted Triple–Promoter Retroviral Vectors and Their Use in Transformation of Primary Mammalian Cells".

Proc. Natl. Acad. Sci. USA, vol. 88, Jun. 1991, pp. 4626–4630, Scharfmann et al., "Long–term in vivo expression of retrovirus–mediated gene transfer in mouse fibroblast implants".

Gene Therapy, 1994, pp. 307–316, Vile et al., "A comparison of the properties of different retroviral vectors containing containing the murine tyrosinase promoter to achieve transcriptionally targeted expression of the HSVtk or IL–2 genes".

Virology vol. 171, 1989, pp. 331–341, Lixu et al., "Factors Affecting Long–Term Stability of Moloney Murine Leukemia Virus–Based Vectors".

Proc. Natl. Acad. Sci. USA, vol. 84, Aug. 1987, pp. 5197–5201, Jiing–Kuan Yee et al., "Gene expression from transcriptionally disabled retroviral vectors".

AIDS. vol. 6 1995, pp. S19–S32, Bryan R. Cullen, "Regulation of HIV gene expression".

* cited by examiner

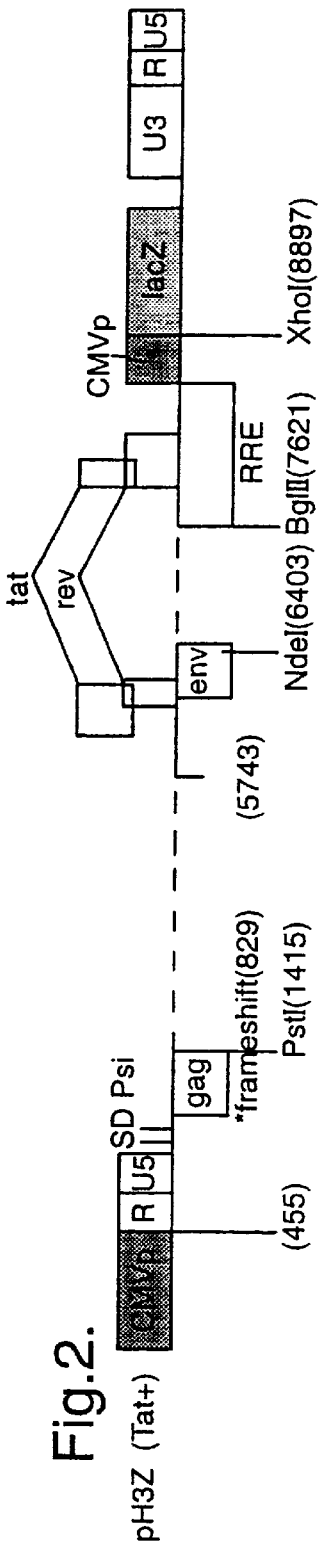
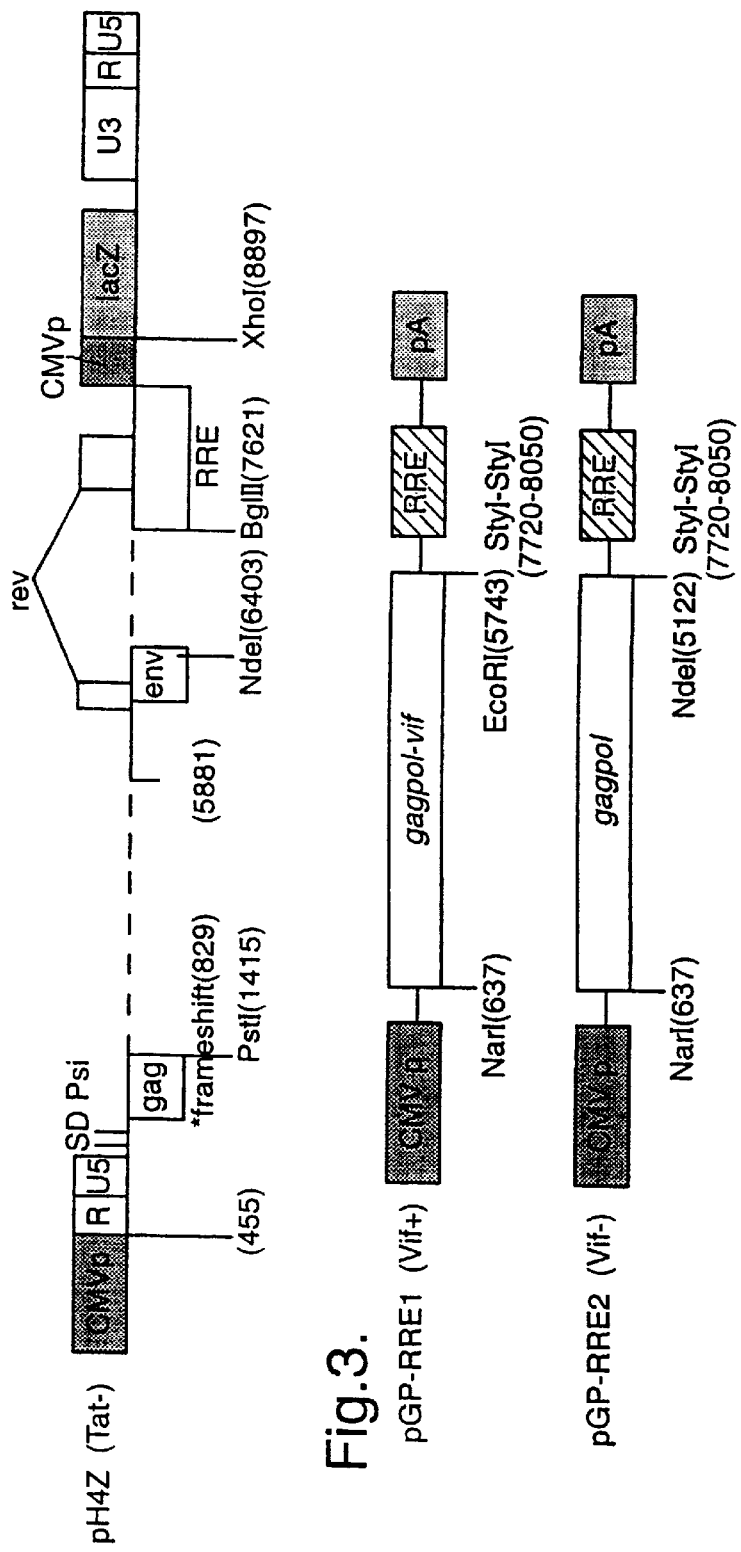
Fig. 2.
Fig. 3.

Fig.4.
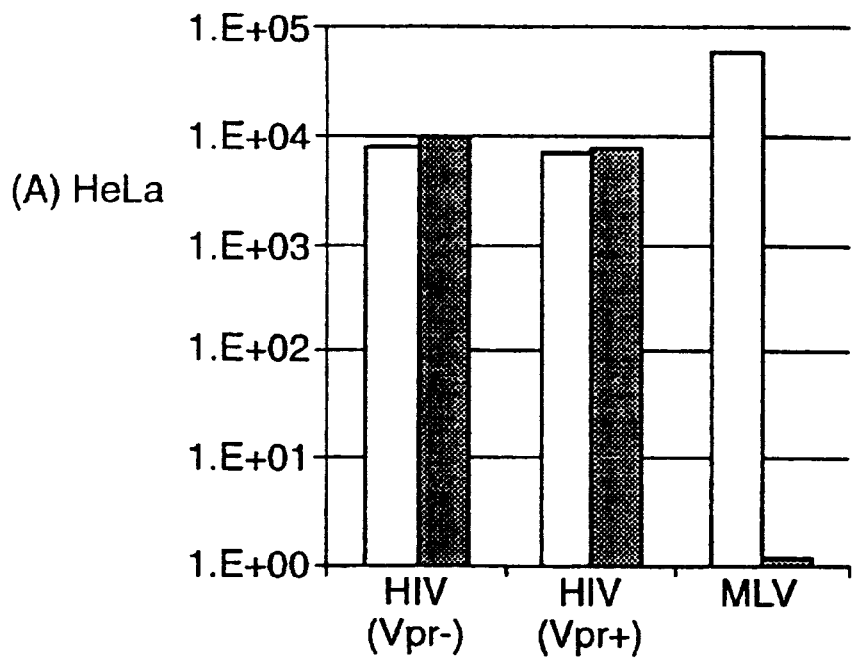
(A) HeLa
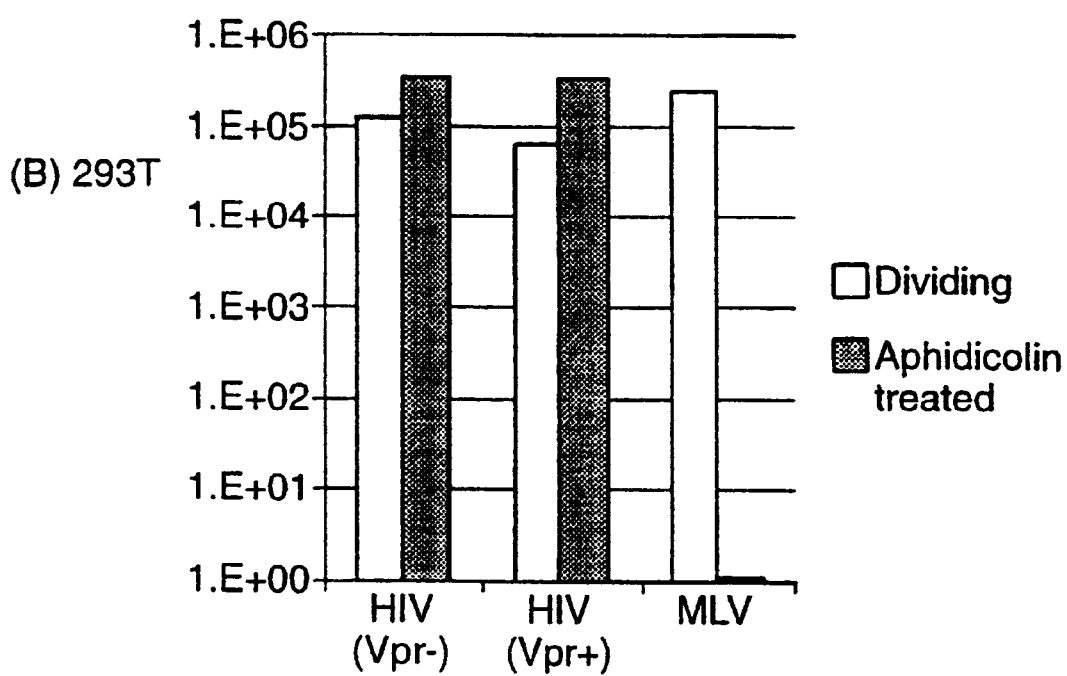
(B) 293T
□ Dividing
▨ Aphidicolin treated

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: oligonucleotide

<400> SEQUENCE: 1
cgtgaattcg cctaaaactg cttgtacca                              29

<210> SEQ ID NO 2
<211> LENGTH: 21
<212> TYPE: DNA
<213> ORGANISM: Artificial Sequence
<220> FEATURE:
<223> OTHER INFORMATION: oligonucleotide

<400> SEQUENCE: 2
gaactaatga ccccgtaatt g                                      21

<210> SEQ ID NO 3
<211> LENGTH: 38
<212> TYPE: DNA
<213> ORGANISM: Artificial Sequence
<220> FEATURE:
<223> OTHER INFORMATION: oligonucleotide

<400> SEQUENCE: 3
gcgaattcgg atccaccatg gaacaagccc cagaagac                    38

<210> SEQ ID NO 4
<211> LENGTH: 36
<212> TYPE: DNA
<213> ORGANISM: Artificial Sequence
<220> FEATURE:
<223> OTHER INFORMATION: oligonucleotide

<400> SEQUENCE: 4
gcgaattcgg atcctctagg atctactggc tccatt                      36

RETROVIRAL VECTORS

This application is a continuation of international application No. PCT/GB97/02857, filed Oct. 17, 1997.

This invention relates to retroviral vector production systems and to retroviral vector particles produced by the systems. In particular, it relates to systems and vector particles from which certain retroviral auxiliary factors are absent. The invention also relates to uses of retroviral vectors, in particular for gene therapy.

Retroviral vectors have been the vehicle of choice for clinical gene transfer because of their efficacy, safety, and stable long-term gene expression. According to the United States National Institutes of Health RAC report issued in September 1996 (Ross et al., 1996), 76 out of 107 trials reviewed by the NIH were based on vector systems derived from the murine leukaemia virus (MLV).

One major drawback of these vectors is their inability to infect non-proliferating cells such as neurons, macrophages and haematopoeitic stem cells. These cells are important targets for gene therapy.

Human immunodeficiency virus type 1 (HIV-1) belongs to a sub-family within the retroviruses, the lentiviruses and in common with other members of this family HIV can infect quiescent cells. This makes lentiviruses attractive vectors for gene therapy.

The viral determinants for HIV-1 infection of non-dividing cells are thought to reside in the p17 matrix protein (MA) and vpr (Gallay et al., 1996). MA has karyophilic properties conferred by a conserved stretch of basic residues, which constitute a nuclear localization signal (NLS) (Bukrinsky et al., 1993). Vpr also contains a distinct NLS (Mahalingam et al., 1995). MA-NLS mutant viruses fail to replicate efficiently in macrophages in the absence of a functional vpr gene (Heinzinger et al., 1994). These data have been interpreted to mean that vpr as well as MA function as karyophilic determinants of HIV-1. In the absence of vpr the transduction efficiency of monocyte-derived macrophages decreases by over 50%, in the presence of functional MA. (Naldini et al., 1996).

Following work reported in Lever et al., 1989 which showed the sequences required for packaging of HIV-1, there has been much interest in the development of an HIV-1 based gene therapy vector. Transfer of foreign genes into a human T-cell line by a replication defective HIV-1 based vector was demonstrated by Poznanski et al (Poznansky et al., 1991). Other groups have designed HIV-1 based vectors that are tat-inducible (Buchschacher, Jr. and Panganiban, 1992) or that use heterologous promoters (Shimada et al., 1991). However, the viral titers obtained with these vectors was low (at most $10^3$ infectious particles per ml), and it was not clear whether the vector system could guarantee the production of helper virus-free vectors. More recently, new efforts to produce helper virus-free vectors have been based on three-plasmid cotransfections (Richardson et al., 1995). HIV vectors can be pseudotyped with Vesicular Stomatitis Virus glycoprotein (VSV-G) and these particles retain infectivity after concentraton by ultracentrifugation (Akkina et al., 1996). Pseudotyping with VSV-G confers a broader host range and eliminates the chances of recombination to produce wild type HIV envelope. In vivo transduction of non-dividing neuronal cells has been demonstrated with VSV-G pseudotyping of HIV-1 in a three-plasmid cotransfection system (Naldini et al., 1996 and Naldini et al., 1996a).

HIV-1 contains nine genes, three of which: gag, pol and env are found in all retroviruses. These are the structural genes. The other six: vif, vpu, vpr, nef, tat and rev are referred to as auxiliary genes. Other retroviruses have different sets of auxiliary genes in their wild type genomes. Some of the auxiliary genes of other retroviruses are analogous to those of HIV-1, although they may not always have been given the same names in the literature. Analogous auxiliary genes have homology in their nucleotide sequences and perform the same or similar functions. HIV-2 and SIV strains generally contain env, vpr, vif, tat, and nef genes analogous to those of HIV1. HIV-2 and some strains of SIV also contain vpx which, in some SIV strains lacking vpr can be considered analogous to vpr. Lentiviruses other than HIV-1 also contain auxiliary genes which are not analogous to the HIV-1 auxiliary genes. Retrovirus auxiliary genes are reviewed for example by Tomonaga and Mikami (1996) and by Joag et al. in Fields Virology, Vol 2.

To date all vector systems based on HIV contain some or all of the HIV auxiliary genes. Rev acts as an RNA export protein and tat is a major transactivator of the proviral long terminal repeat (LTR). The auxiliary genes play a crucial role in viral replication and pathogenesis. The auxiliary genes have not been fully characterized nor their function defined.

However some of the auxiliary genes are thought to be involved in the pathogenesis of HIV-1. Tat has been implicated in the development of Kaposi's sarcoma (Barillari et al., 1993; Ensoli et al., 1990). HIV vpr has been shown to cause cell arrest and apoptosis and this has been proposed to be the cause of T-Cell dysfunction seen in AIDS patients (Jowett et al., 1995). Also extracellular Vpr present in peripheral blood has been suggested to contribute to tissue-specific pathologies associated with HIV infection since Vpr induces cell proliferation and differentiation (Levy et al, 1993 and Levy et al, 1995).

Since the roles of the auxiliary genes are not clear and they probably play a major role in pathogenesis their removal from HIV-1 vector production systems is desirable, provided that sufficiently high retrovirus vector titer and ability to transduce non-proliferating cells can be retained.

Naldini et al's data shows that the presence or absence of vpu has no effect on the vector particle titer. That is, a packaging system they used produced a titer of $4 \times 10^5$ when pseudotyped with VSV-G and this system was env and vpu negative. In another system which was only env negative they obtained the same titer (Naldini et al. 1996 and Naldini et al. 1996a). However, as already discussed another system of Naldini et al which was vpr negative as well as vpu negative gave a transduction efficiency which was decreased by 50% compared to a vpr positive system.

We have now discovered that leaving some or all of the auxiliary genes out of retrovirus vector production systems does not significantly compromise vector particle titers or the ability of the vector verticles to transduce non-dividing cells.

The invention therefore provides in one aspect a retroviral vector production system for producing lentivirus-based, replication defective vector particles for gene therapy, said vector particles capable of infecting and transducing non-dividing mammalian target cells, which system comprises a set of nucleic acid sequences encoding the components of the vector, wherein one or more functional genes chosen from the HIV-1 auxiliary genes vpr, vif, tat and nef or from the analogous auxiliary genes of other lentiviruses, which auxiliary genes are normally present in the lentivirus on which the vector particles are based, is or are absent from the system. The functional vpu gene may also be absent, with the proviso that when the production system is for an HIV-1 based vector and vpr and vpu are both absent, so also is one of the other auxiliary genes.

In another aspect, the invention provides retroviral vector particles produced by a retroviral vector particle production system described herein.

In yet another aspect, the invention provides a DNA construct for use in a retroviral vector production system described herein, said DNA construct encoding a packagable RNA vector genome for a retroviral vector particle and operably linked to a promoter, wherein all of the functional retroviral auxiliary genes are absent from the construct, other than rev which is optionally present. The DNA construct may be provided as part of a set of DNA constructs also encoding some or all of the structural components of the vector particles.

In further aspects, the invention provides the use of retroviral vector particles as described herein, for gene therapy and in the preparation of a medicament for gene therapy; and a method of performing gene therapy on a target cell which method comprises infecting and transducing the target cell using a retroviral vector particle as described herein. The invention further provides transduced target cells resulting from these uses and methods. The invention thus provides a gene delivery system for use in medicine.

The expression "lentivirus-based" means that the vector particles are derived from a lentivirus. The genome of the vector particle comprises components from the lentivirus as a backbone. The vector particle as a whole contains essential vector components compatible with the RNA genome, including reverse transcription and integration systems. Usually these will include the gag and pol proteins derived from the lentivirus.

Being derived from a lentivirus, the retroviral vector particles are capable of infecting and transducing non-dividing cells. Thus, the vector particles are able to deliver a selected gene or genes such as therapeutically active genes, to the genome of a target cell. During the infection process, lentiviruses form a pre-integration complex in the target cell cytoplasm containing integrase, core proteins and proviral DNA. The complex is able to pass across the nuclear membrane of the target cell, by means of signal sequences in the proteins. Non-lentiviral retroviruses either lack the proteins or have the proteins but without the appropriate signal sequences.

Examples of lentiviruses are HIV-1 and HIV-2, SIV, FIV, BLV, EIAV, CEV and visna virus. Of these, HIV and SIV are presently best understood. However, a non-immunodeficiency virus may be preferred for use in gene therapy because the immunodeficiency viruses inevitably bring with them safety considerations and prejudices.

The absence of functional auxiliary genes from the retroviral vector production system means that those functional genes will also be absent from retroviral vector particles produced by the system. Also, any auxiliary proteins that would otherwise be encoded by those genes and incorporated into the vector particles, will be absent from the vector particles. In known retroviral vector production systems, the auxiliary genes may be present as part of the vector genome-encoding DNA, or together with the packaging components. The location of an auxiliary gene in a vector production system depends in part on its relationship with other retroviral components. For example, vif is often part of a gag-pol packaging cassette in a packaging cell. Thus, to remove a functional auxiliary gene for the purposes of the invention may involve its removal from the packaging components, or from the vector genome, or perhaps both.

To remove a functional auxiliary gene may not require removal of the gene in its entirety. Usually removal of part of the gene, or disruption of the gene in some other way will be sufficient. The absence of a functional auxiliary gene is understood herein to mean that the gene is not present in a form in which it is capable of encoding the functional auxiliary protein.

In a preferred system according to the invention, functional vpr and tat genes or analogous genes normally present in the lentivirus on which the vector particles are based are both absent. These two auxiliary genes are associated with characteristics of lentiviruses which are particularly undesirable for a gene therapy vector. However, other than by the proviso given above, the invention is not limited with regard to the combination of auxiliary genes that are absent. In a system according to the invention for producing HIV-1-based vector particles, any combination of three, or more preferably four, of the genes may be absent in their functional form. Most preferably, all five of the auxiliary genes vpr, vif, tat, nef, and vpu are absent in their functional form. Similarly, for systems concerned with other lentiviruses, it is most preferable that all of the auxiliary genes are absent in their functional form (except rev which is preferably present unless replaced by a system analogous to the rev/RRE system).

In order to ensure efficient export of RNA transcripts of the vector genome from the nucleus to the cytoplasm, it is preferable to include functional rev and rev response element (RRE) sequences in the vector genome, or to include alternative sequences in the genome which perform the same function as the rev/RRE system. For example, a functional analogue of the rev/RRE system is found in Mason Pfizer monkey virus. This is known as CTE and consists of an RRE-type sequence in the genome which is believed to interact with a factor in the infected cell. The cellular factor can be thought of as a rev analogue. Thus, CTE may be used as an alternative to the rev/RRE system.

As will be evident, in order to function as a vector the retroviral vector particles described herein will need to have a reverse transcription system (compatible reverse transcription and primer binding sites) and an integration system (compatible integrase and integration sites) allowing conversion to the provirus and integration of the double-stranded DNA into the target cell genome. Additionally, the vector genome will need to contain a packaging signal. These systems and signals will generally be derived from the lentivirus on which the vector is based. It will be evident that although the vector according to the invention is based on a lentivirus, the elements of the lentivirus incorporated into the vector may be genetically or otherwise altered versions of the elements in the wild type lentivirus. Alterations may be achieved by manipulating either the RNA genome or other components of the retroviral vector particle production system. For example, portions of the lentivirus genome not required for the vector can be excluded. Also, the vector production system can employ substitutes e.g. for the lentivirus env gene, to give the vector a different target cell range (this is known as pseudotyping).

A retroviral vector particle according to the invention carries one or more selected genes for delivery to a target cell. The selected genes are chosen according to the effect sought to be achieved. For gene therapy purposes there will be at least one therapeutically active gene encoding a gene product which is active against the condition it is desired to treat or prevent. Additionally there may be a selected gene which acts as a marker by encoding a detectable product. Therapeutic genes may encode for example an antisense RNA, a ribozyme, a transdominant negative mutant of a target protein, a toxin, a conditional toxin, an antigen that induces antibodies or helper T-cells or cytotoxic T-cells, a single chain antibody or a tumour suppressor protein.

Preferably the construction of the vector genome is such that in the DNA provirus, the therapeutic gene or genes is or are under transcriptional control of the 5' LTR but not otherwise operably linked to any other promoter from the vector. Thus, expression of the gene or genes is in a single transcription unit. Preferably also the 5' LTR is a modified lentivirus LTR for which the promoter function is not tat-dependent. This may be achieved by replacing the R and U3 lentivirus promoter functions by alternative promoter functions, which may be derived from another retrovirus or may be of non-retroviral origin. A strategy for this is described in Cannon et al 1996 and in the Examples.

It will be evident that the term "gene" is used loosely here, and includes any nucleic acid coding for the desired polypeptide or RNA. Usually, genes delivered by vectors according to the invention will be cDNAs.

Retroviral vector particles according to the invention will also be capable of infecting and transducing cells which are slowly-dividing, and which non-lentiviruses such as MLV would not be able to efficiently infect and transduce. Slowly-dividing cells divide once in about every three to four days. Mammalian non-dividing and slowly-dividing cells include brain cells, stem cells, terminally differentiated macrophages, lung epithelial cells and various other cell types. Also included are certain tumour cells. Although tumours contain rapidly dividing cells, some tumour cells especially those in the centre of the tumour, divide infrequently.

The DNA construct encoding the vector genome described wherein is preferably linked to a high efficiency promoter such as the CMV promoter. Other high efficiency promoters are known. This gives rise to a high level of expression of the vector RNA by the retroviral vector production system.

Suitable host or producer cells for use in the retroviral vector production system according to the invention are well known in the art. Many retroviruses have already been split into replication defective genomes and packaging components. For those which have not the technology is available for doing so. The producer cell encodes the viral components not encoded by the vector genome such as the gag, pol and env proteins. The gag, pol and env genes may be introduced into the producer cell and stably integrated into the cell genome to give a packaging cell line. The retroviral vector genome is then introduced into the packaging cell line by transfection or transduction to create a stable cell line that has all of the DNA sequences required to produce a retroviral vector particle. Another approach is to introduce the different DNA sequences that are required to produce a retroviral vector particle e.g. the env coding sequence, the gag-pol coding sequence and the defective retroviral genome into the cell simultaneously by transient triple transfection. In a preferred system according to the invention, both the structural components and the vector genome will all be encoded by DNA stably integrated into a host cell genome.

In the attached figures:

FIG. 2 shows HIV-based vector genomes for use in the invention;

FIG. 3 shows HIV-1 gag-pol gene expression plasmids for use in the invention; and FIG. 4 shows transduction efficiencies for vectors according to the invention lacking the five auxiliary factors.

Figure 1:
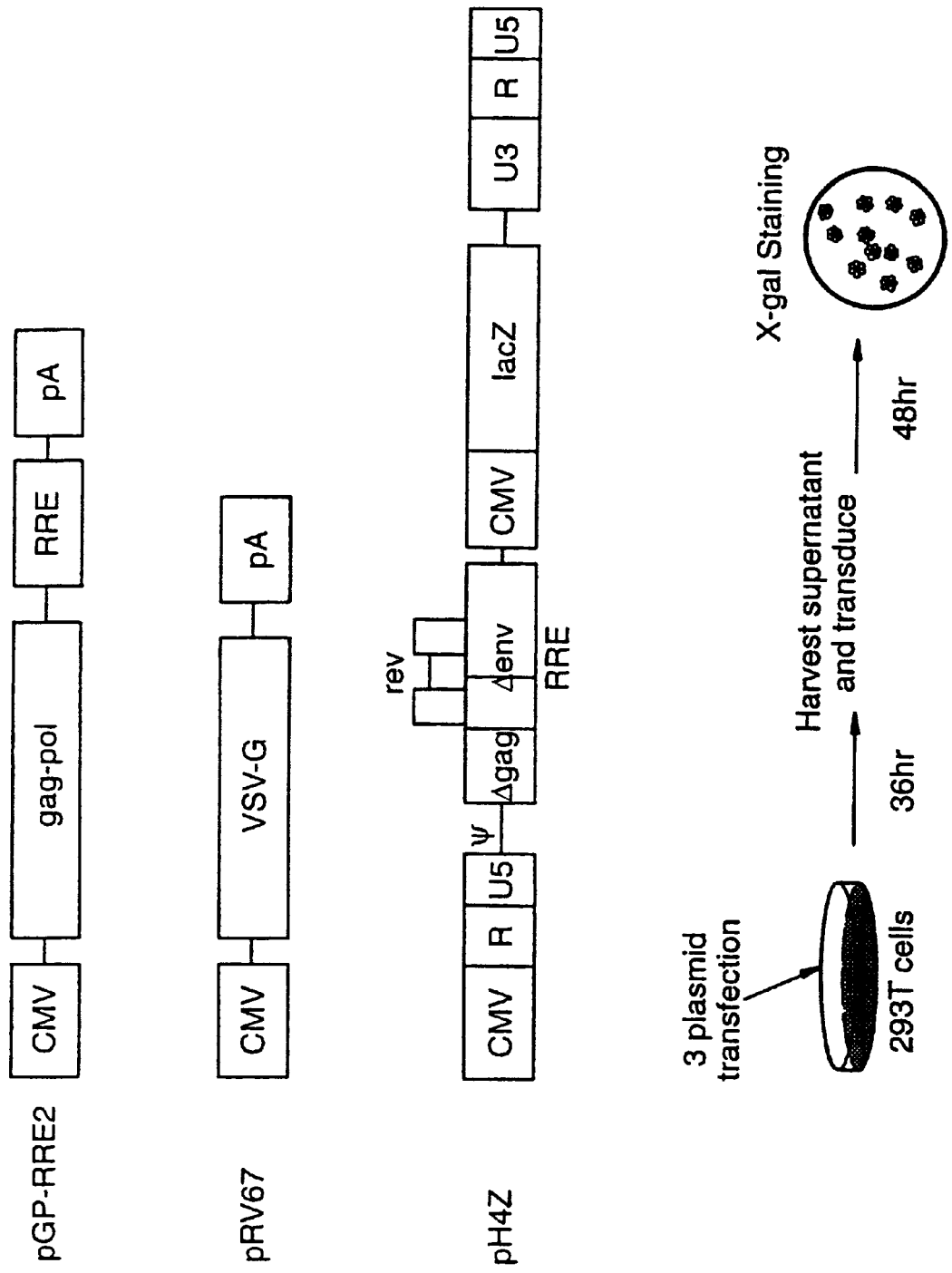
FIG. 1 shows a vector production system according to the invention, using a three-plasmid co-transfection of 293T cells.

To produce a safe HIV packaging system devoid of all unnecessary genes, we have developed a system which does not contain vpr, nef, tat, vif or vpu (FIG. 1.). The packaging components were placed on three separate plasmids and overlapping sequences were minimised ensuring no recombination and no helper virus production. This HIV vector has been shown to transduce aphidicolin treated non-dividing cells in the absence of vpr. Titers were obtained that are similar to the Naldini et al titers for systems which contain all the auxiliary genes (Naldini et al. 1996a).

This is the first minimal lentiviral vector system. The fact that high titers are observed with this system shows that the auxiliary genes (except rev) are redundant for the production of high titers and for the transduction of non-dividing cells. This is contrary to the assumption made by Naldini et al that the reason for the production of high titer virus stocks is due to the incorporation of accessory proteins (such as nef) into the viral particle (Naldini et al 1996).

The system may have additional advantages for HIV therapy. Replacing the HIV-1 LTR with a different promoter such as a constitutive HCMV promoter permits the use of anti-Tat molecules such as Tat transdominant mutants (Echetebu et al, 1994) or TAR decoys (Lisziewicz et al, 1993) as therapeutic agents as they will not affect vector production.

It will be evident that minimal lentiviral vectors as described herein, lacking all of the wild-type virus auxiliary genes, may also have applications as vaccines.

EXAMPLES

Materials and Methods

Plasmid Construction pGP-RRE1 is a pWl3 (Kim et al., 1989) derived gagpol vif expression plasmid. The RRE of pWl3 (Accession number: U26942) was inserted by blunt-ending the Sty I/Sty I fragment (7720–8050) into pBluescript KS+ Sma I cut creating pBSRRE. The Nar I/Eco RI fragment of pWl3 (637–5743) was inserted into pBSRRE cut with Cla I and Eco RI to create pBSGPRRE1. The Xho I/Not I fragment (containing gagpol and RRE) was inserted into the expression plasmid pCI-Neo to create pGR-RRE1. To remove the vif coding region, pBSGPRRE1 was cut with NdeI and SmaI, blunt-ended and was relegated to generate pBSG-PRRE2. The gagpol gene and RRE were inserted into pCI-neo in XhoI and NotI site to make pGP-RRE2.

The construction of pTIN406, pTIN408 and pTIN414 has been described (Cannon et al., 1996). The 5' LTR of pH3Z and pH4Z contain a CMV promoter at the U3 position and the HIV R and U5 regions. HIVdge was made from HIVgpt (Page et al., 1990) by blunt-ending the Cla I site (829) to create a frameshift mutation. HIVdge was cut with Bgl II and Pst I (473–1414) and inserted into pTIN406. pTIN406 has an LTR structure of CMV, R (HIV) and U5 (MLV). This created a hybrid LTR containing CMV, and R, U5 from HIV called pBS5'. To provide the plasmid with rev and RRE the Eco RI/Xho I fragment (5743–8897) was cut from HIVdge1.2 which is a HIVdge derivative containing a deletion from Nde I to Bgl II (6403–7621) and was inserting into pBS5' to create pBS5'R. The 3' LTR was provided by inserting the Not I/Xho I fragment of pBS3' into pBS5'R creating pH2. pBS3' was created by a three way ligation of the Xho I/Hind III fragment of pWl3, the Hind III/Kpn I fragment of pTIN408 into pBluescript KS+ (Xho I/Kpn I). A CMV promoter was inserted into the unique Xho I site of pH2 from pSPCMV (Sal I/Xho I) making pH2CMV.

pSPCMV was created by inserting pLNCX (Accession number: M28246) (Pst I/Hind III) into pSP72 (Promega). The β-galactosidase gene was inserted from PTIN414 into pSP72 (Xho I/Sph I) to make pSPlacZ. A Xho I/Sal I digest of pSPlacZ gave the β-galactosidase coding region which was inserted into pH2-CMV to give pH3Z. pH4Z was constructed to create tat-deficient vector. The first 50 bp of the tat-coding region was removed by replacing EcoRI (5743)I-Spel fragment in pH3 with EcoRI (5881)-Spel PCR product amplified using PCR primers DELT5 (5'-CGTGAATTCGCCTAAAACTGCTTGTACCA-3') and DELT3 (5'-GAACTAATGACCCCGTAATTG-3') to create pH4. The Nsi I/Spe I fragment from pH4 was inserted into pH3Z to generate pH4Z.

A vpr expression plasmid was constructed by PCR amplification of the vpr coding region from pNL4.3 (Accession number: U26942) using the following primers: 5' primer GCGAATTCGGATCCACCATGGAACAAGC-CCCAGAAGAC (5563–5583) and 3' primer GCGAAT-TCGGATCCTCTAGGATCTACTGGCTCCATT (5834–5853). This amplicon was cloned into pLIGATOR (R & D Systems). The expression plasmid pCl-vpr was made by inserting the Mlu I and Xho I fragment containing the vprcoding region into pCl-Neo (Promega).

pAC29.1 was cut by Bam HI to give the VSV-G coding region which was inserted into pSA91 (Bgl II).

Cell Lines 293T (293ts/A1609) (DuBridge et al., 1987) cells were maintained in Dulbelco's modified Eagle's medium (GIBCO), HeLa cells and 208F cells in MEM (GIBCO), all of which containing 10% (v/v) fetal calf serum supplemented with antibiotics.

Production and Assays of Vectors

Retroviral vector stocks were produced according to our previously published protocol (Soneoka et al, 1995). Briefly, human kidney 293T (1.5×10⁶) cells were plated on 10-cm plates and transiently transfected with 15 mg of each plasmid (gag-pol and env expression plasmids together with a vector plasmid) by calcium phosphate DNA precipitation (Chen and Okayama, 1987). The culture supernatants were harvested 36 hours later, filtered through 0.45 mm and either used immediately or frozen at −70° C. Transduction was carried out by adding virus onto target cells for 2 hours, in the presence of 8 mg/ml polybrene followed by the addition of fresh media. 5-bromo-4-chloro-3-indolyly b-D-galactoside (X-Gal) was used to measure the expression of β-galactosidase 48 hours later, as previously described (Soneoka et al., 1995). Titers were obtained by counting the number of lac z (blue foci) forming units per ml (l.f.u./ml). G1/S phase arrested cultures were prepared by adding aphidicolin (5 mg/ml) 24 hours before infection and then daily throughout the experiment.

Results

HIV Vector Production

H3Z (tat positive) and H4Z (tat negative) are HIV-1 based vectors designed to be produced by three plasmid co-transfection into 293T cells (FIG. 2). For efficient packaging by the HIV cores, the vectors contain the first 778 bases of gag but a frameshift mutation, introduced 40 bp from the ATG start codon, prevents the expression of gag proteins. RRE was included to boost packaging efficiency and rev is expressed from the vector to support the HIV mRNA export. The internal CMV promoter-driven β-galactosidase gene was inserted to serve as a reporter gene. For both the vector genomes transcription is driven by a CMV promoter which has been used to replace the 5' LTR U3. This makes the vector genome tat independent. Two HIV-1 gagpol constructs were made (FIG. 3); pGP-RRE1 (vif positive) and pGP-RRE2 (vif negative). Since the gagpol genes have been inserted into pCl-neo which is a CMV driven expression plasmid gagpol expression is tat independent. pRV67, the VSV glycoprotein construct was used for the pseudotyping. By placing the different genes on different plasmids the probability of generating replication competent virus by recombination could be minimized.

Transduction Efficiency of the Vector

Replication defective retroviral particles were generated by transient co-transfection of human kidney 293T cells with the three plasmids described above and either used immediately or frozen at −70° C. The different vector constructs were used to produce virus. It was found that the minimal constructs (H4Z and pGP-RRE2) gave comparable titers to that of the vif, vpr, nef and tat positive viruses (Table 1).

When the minimal system was tested on various cell lines the titers differed (Table 2). The vectors yielded titers of $3.2 \times 10^5$ l.f.u./ml with polybrene treatment, $9.1 \times 10^4$ l.f.u./ml without polybrene treatment in 293T cells. Also the same vectors, without polybrene, yielded $9.6 \times 10^3$ l.f.u./ml and $8.3 \times 10^3$ l.f.u./ml in HeLa and 208F cells, respectively. These titers are comparable with those obtained by Naldini et al., 1996 (Naldini et al., 1996), which are the highest ones published so far.

Effect of vpr on the Transduction of Aphidicolin-treated Cells

To test the effect of vpr on non-dividing cell transduction, vpr was included in the packaging system by co-transfection of pCl-vpr along with pH4Z, pGP-RRE2 and pRV67 plasmids. The transduction efficiencies of the viral particles generated were assayed on growing and growth-arrested 293T cells and HeLa cells (FIG. 4). MLV-derived packaging and transducing vectors (Soneoka, 1995) served as controls. HeLa cells and 293T cells were growth-arrested at G1/S phase by aphidicolin treatment. The minimal HIV vector H4Z was as efficient at transducing G1/S-arrested as proliferating HeLa and 293T cells, whereas the MLV-based vector was only 0.002% as effective.

Vpr-deficient H4Z could transduce the growth-arrested cells as efficiently as vpr-containing vector, suggesting that HIV-1 MA is sufficient for providing the vector with the ability to transduce non-dividing cells.

Conclusion

We have set up an HIV-1 based vector production system, which does not contain vpr, vpu, nef, vif and tat based on a three-plasmid co-transfection method. This vector can transduce proliferating cells with a titer of up to $3.2 \times 10^5$ l.f.u./ml, which is comparable to other MLV-based vectors and can easily be increased by concentration using ultracentrifugation (data not shown). No helper virus has been detected (data not shown).

This minimal vector has been demonstrated to transduce growth-arrested HeLa cells and 293T cells as efficiently as vpr, vif, nef and tat containing vectors. Therefore it can be concluded that only rev is required for the production of high titer HIV based vectors and that these vectors can transduce non-dividing cells.

This is the first report of the construction of a high titer minimal lentiviral vector that can transduce non-dividing cells. The removal of five out of the six auxiliary genes (except rev) and the minimal sequence overlap between the plasmids makes this system the safest one to date for the production of HIV-vectors for gene therapy.

Figure Legends

FIG. 2. HIV vector genomes. The numbers indicate the coordinates from HXB2. HCMV promoter (−597 to −1). HIV sequences (455 to 1415; 5743 (H3Z) or 5881 (H4Z) to 6403; 7621 to 8897; 8897 to 9720) from HXB2. HCMV promoter as an internal promoter (900 bp). Cloning site (XhoI). Backbone; pBluescriptKS+.

FIG. 3. HIV-1 gag-pol gene expression plasmids. HIV-1 gagpol coding region and RRE was cloned into pCl-neo (PROMEGA) at XhoI and NotI site.

FIG. 4. Transduction of non-dividing cells. Transduction efficiencies of the H4Z vectors were measured by X-gal staining and are shown in Y-axis as l.f.u./ml. G1/S phase arrested cells were prepared by treating the cells with aphidicolin (5 µg/ml).

References

Akkina, R. K., Walton, R. M., Chen, M. L., Li, Q. X., Planelles, V., and Chen, I. S. (1996). J. Virol. 70, 2581–2585.

Barillari, G., Gendelman, R., Gallo, R. C., and Ensoli, B. (1993). Proc. Natl. Acad. Sci. U. S. A. 90, 7941–7945.

Buchschacher, G. L., Jr. and Panganiban, A. T. (1992). J. Virol. 66, 2731–2739.

Bukrinsky, M. I., Haggerty, S., Dempsey, M. P., Sharova, N., Adzhubel, A., Spitz, L., Lewis, P., Goldfarb, D., Emerman, M., and Stevenson, M. (1993). Nature 365, 666–669.

Cannon, P. M., Kim, N., Kingsman, S. M., and Kingsman, A. J. (1996). J. Virol. 70, 8234–8240.

Chen, C. and Okayama, H. (1987). Mol. Cell Biol. 7, 2745–2752.

Echetebu, C. O., H. Rhim, C. H. Herrmann and A. P. Rice (1994), J. Acquired Immune Defic. Syndrome. 7, 655–664.

Ensoli, B., Barillari, G., Salahuddin, S. Z., Gallo, R. C., and Wong Staal, F. (1990). Nature 345, 84–86.

Gallay, P., Stitt, V., Mundy, C., Oettinger, M., and Trono, D. (1996). J. Virol. 70,1027–1032.

Heinzinger, N. K., Bukinsky, M. I., Haggerty, S. A., Ragland, A. M., Kewalramani, V., Lee, M. A., Gendelman, H. E., Ratner, L., Stevenson, M., and Emerman, M. (1994). Proc. Natl. Acad. Sci. U. S. A. 91, 7311–7315.

Joag, S. V., Stephens, E. B. and Narayan, O. in Fields Virology, Vol 2, 1970–1982 (Lippincott-Raven Publishers).

Jowett, J. B., Planelles, V., Poon, B., Shah, N. P., Chen, M. L., and Chen, I. S. (1995). J. Virol. 69, 6304–6313.

Kim, S. Y., Byrn, R., Groopman, J., and Baltimore, D. (1989). J. Virol. 63, 3708–3713.

Lever, A., Gottlinger, H., Haseltine, W., and Sodroski, J. (1989). J. Virol. 63, 4085–4087.

Levy, D. N., L. S. Fernandes, W. V. Williams, and D. B. Weiner (1993), Cell, 72, 541–50.

Levy, D. N., Y. Refae; and D. B. Weiner (1995), J. Virol., 69,1243–52.

Lisziewicz, J., D. Sun, J. Smythe, P. Lusso, F. Lori, A. Louie, P. Markham, J. Rossi, M. Reitz and R. C. Gallo (1993), Proc. Natl. Acad. Sci, USA, 90, 8000–4.

Mahalingam, S., Collman, R. G., Patel, M., Monken, C. E., and Srinivasan, A. (1995). Virology 212, 331–339.

Naldini, L., Blomer, U., Gallay, P., Ory, D., Mulligan, R., Gage, F. H., Verma, I. M., and Trono, D. (1996). Science 272, 263–267.

Naldini, L., Blomer, U., Gage, F. H., Trono, D., and Verma, I. M. (1996). Proc. Natl. Acad. Sci. U. S. A. 93, 11382–11388.

Page, K. A., Landau, N. R., and Littman, D. R. (1990). J. Virol. 64, 5270–5276.

Poznansky, M., Lever, A., Bergeron, L., Haseltine, W., and Sodroski, J. (1991). J. Virol. 65, 532–536.

Richardson, J. H., Kaye, J. F., Child, L. A., and Lever, A. M. (1995). J. Gen. Virol. 76, 691–696.

Ross, G., Erickson, R., Knorr, D., Motulsky, A. G., Parkman, R., Samulski, J., Straus, S. E., and Smith, B. R. (1996). Hum. Gene Ther. 7, 1781–1790.

Shimada, T., Fujii, H., Mitsuya, H., and Nienhuis, A. W. (1991). J. Clin. Invest. 88, 1043–1047.

Tomonaga, K. and Mikami, T. (1996). J. General Virol. 77, 1611–1621.

TABLE 1

Effects of accessory gene expression on vector titer.

| Accessory genes | | | | Plasmids | | | | Titer |
| --- | --- | --- | --- | --- | --- | --- | --- | --- |
| Tat | Vif | Nef | Vpr | Vector | Gagpol | Nef | Vpr | (l.f.u./ml)[a] |
| + | + | − | + | pH3Z | pGP-RRE1 | | pCl-Vpr | 2.2 × 10$^5$ |
| + | + | + | − | pH3Z | pGP-RRE1 | pC-Nef | | 2.5 × 10$^5$ |
| + | + | − | − | pH3Z | pGP-RRE1 | | | 4.0 × 10$^5$ |
| + | − | − | − | pH3Z | pGP-RRE2 | | | 3.7 × 10$^5$ |
| − | − | − | − | pH4Z | pGP-RRE2 | | | 4.6 × 10$^5$ |

[a]Transduction efficiency was measured in 293T cells by counting the number of blue colonies following X-gal staining 48 hours after transduction and were indicated as lacZ colony forming unit per ml virus stock (l.f.u./ml).

TABLE 2

Transduction efficiency of the minimal H4Z vector on various cell lines.

| | | Titer (l.f.u./ml)[a] | |
| --- | --- | --- | --- |
| Cell line | | Without polybrene | With polybrene |
| 293T | Human kidney | 9.1 × 10$^4$ | 3.2 × 10$^5$ |
| HeLa | Human epithelium | 9.6 × 10$^3$ | N.D. |
| 208f | Rat fibroblast | 8.3 × 10$^3$ | N.D. |

[a]Transduction efficiency was measured by counting the number of blue colonies following X-gal staining 48 hours after transduction and were indicated as lacZ colony forming unit per ml virus stock (l.f.u./ml).

What is claimed is:

1. An infection and transduction competent, lentivirus-based retroviral vector particle comprising a genome, gag, pol, an envelope protein, and optionally a functionally active rev, wherein the particle lacks all functional lentiviral auxiliary gene products other than the optionally present functionally active rev.

2. An infection and transduction competent, lentivirus-based retroviral vector particle comprising a genome, gag, pol, and an envelope protein, wherein the particle lacks all functional lentiviral auxiliary gene products; or the particle lacks all functional lentiviral auxiliary gene products, except a functionally active rev.

3. The retroviral vector particle according to claim 1 or 2 wherein the retroviral vector particle further comprises a nucleic acid sequence which encodes one or more genes of interest.

4. The retroviral vector particle according to claim 3 wherein the gene of interest encodes a therapeutic protein.

5. An isolated cell comprising the retroviral vector particle of claim 4.

6. A composition comprising the retroviral vector particle of claim 3 and a carrier.

7. A composition comprising the retroviral vector particle of claim 4 and a carrier.

8. A method for expressing a gene of interest or replicating a nucleic acid molecule therefor comprising contacting a cell with the retroviral vector particle of claim 3.

9. A method for expressing a gene of interest comprising introducing a gene of interest into a cell by contacting said cell with the retroviral vector particle of claim 3.

10. A retroviral vector production system for producing the infection and transduction competent, lentivirus-based retroviral vector particle according to claim 3, which system comprises nucleic acid sequence(s) encoding the genome of the retroviral vector particle, gag, pol, and the envelope protein, and optionally the functionally active rev, wherein all lentiviral auxiliary genes, or all lentiviral auxiliary genes except the optionally present rev, are absent or are disrupted, whereby functional auxiliary proteins encoded by said auxiliary genes are not expressed in the system.

11. A retroviral vector production system for producing infection and transduction competent, lentivirus-based vector particle according to claim 2, which system comprises nucleic acid sequence(s) encoding the genome of the vector particle, gag, pol, and an envelope protein, or the genome of the vector particle, gag, pol, an envelope protein, and a functionally active rev, wherein all lentiviral auxiliary genes, or all lentiviral auxiliary genes except rev, are absent or are disrupted, whereby functional auxiliary proteins encoded by said auxiliary genes are not expressed in the system.

12. The retroviral vector production system according to claim 10 or 11, wherein the nucleic acid sequence encoding the genome of the vector further comprises one or more genes of interest.

13. The retroviral vector production system according to claim 12, wherein the gene of interest encodes a therapeutic protein.

14. The retroviral vector production system according to claim 10 or 11, wherein the nucleic acid sequence(s) include three DNA constructs which encode: the genome of the vector particle, gag and pol proteins, and the envelope protein, respectively.

15. The retroviral vector production system according to claim 10 or 11, wherein the nucleic acid sequence comprises rev and RRE sequences.

16. A retroviral vector particle produced by the system according to claim 10 or 11, wherein the nucleic acid sequence encoding the genome of the vector particle further comprises one or more genes of interest.

17. A method for expressing a gene product comprising introducing a gene of interest into a cell by contacting said cell with the retroviral vector particle according to claim 16.

18. A composition comprising the retroviral vector particle according to claim 16, in a carrier.

19. An isolated cell comprising the retroviral particle of claim 16 on or in the cell.

20. The retroviral vector particle according to claim 16, wherein the gene of interest encodes a therapeutic portion.

21. A method for expressing a gene product comprising introducing a gene of interest into a cell by contacting said cell with the retroviral vector particle according to claim 20.

22. An isolated cell comprising the retroviral particle of claim 20 on or in the cell.

23. An isolated cell comprising the retroviral particle of claim 3 on or in the cell.

24. The retroviral vector particle of any one of claims 1 or 2, wherein the functionally active rev is present.

25. The retroviral vector particle of claim 3, wherein the functionally active rev is present.

26. The retroviral vector particle of claim 4, wherein the functionally active rev is present.

27. The retroviral vector particle of claim 16, wherein the functionally active rev is present.

28. The retroviral production system of any one of claims 10 or 11 wherein the genome includes an operable promoter.

29. The retroviral production system of claim 28 wherein the promoter is a non-retroviral promoter.

30. A set of nucleic acid sequences encoding the components of the infection and transduction competent, lentivirus-basedvector particle according to any one of claims 1 or 2, comprising: a first DNA construct which encodes the genome of the vector particle, a second DNA construct which encodes gag and pol proteins, and a third DNA construct which encodes an envelope protein, wherein: one of the DNA constructs optionally encodes a functionally active rev; and all other lentiviral auxiliary gene products are absent from the retroviral vector particle and producer cells in which the sequences are expressed, and lentiviral auxiliary genes encoding said other lentiviral auxiliary gene products are absent from or disrupted in the set of sequences.

31. The set of nucleic acid sequences of claim 30, wherein the functionally active rev is present.

32. The set of nucleic acid sequences of claim 30 which further comprises one or more genes of interest.

33. The set of nucleic acid sequences of claim 30 wherein the genome includes an operable promoter.

34. The set of nucleic acid sequences of claim 33 wherein the promoter is a non-retroviral promoter.

35. A method for producing the infection and transduction competent, lentivirus-based, replication defective vector particle as claimed in claim 1 or 2, comprising coexpressing in a retroviral producer cell nucleic acid sequence(s) encoding the genome of the vector particle, gag and pol proteins, and an envelope protein, and, optionally a functionally active rev; wherein one of the nucleic acid sequence(s) optionally encodes a functionally active rev; and all other lentiviral auxiliary gene products are absent from the retroviral vector particle and producer cells in which the sequence(s) are expressed, and lentiviral auxiliary genes encoding said other lentiviral auxiliary gene products are absent from or disrupted in the sequence(s).

36. A method for producing the injection and transduction competent, lentivirus-based, replication defective vector particle as claimed in claim 1 or 2, comprising coexpressing in a retroviral producer cell nucleic acid sequence(s) encoding the genome of the vector particle, gag and pol proteins, and an envelope protein; wherein all lentiviral auxiliary gene products are absent from the retroviral vector particle and producer cells in which the sequence(s) are expressed, and lentiviral auxiliary genes encoding said lentiviral auxiliary gene products are absent from or disrupted in the sequence(s).

37. A method for producing the infection and transduction competent, lentivirus-based, replication defective vector particle according to claim 1 or 2, consisting essentially of coexpressing in a retroviral producer cell nucleic acid sequence(s) encoding the genome of the vector particles, gag and pol proteins, and an envelope protein.

38. The method of claim 35 wherein the nucleic acid sequence(s) include one or more genes of interest.

39. The method of claim 36 wherein the nucleic acid sequence(s) include one or more genes of interest.

40. The method of claim 37 wherein the nucleic acid sequence(s) include one or more genes of interest.

41. The method of claim 35 wherein the coexpressing is of: a first DNA construct which encodes the genome of the vector particles, a second DNA construct which encodes gag and pol proteins, and a third DNA construct which encodes the envelope protein, wherein one of the DNA constructs optionally encodes a functionally active rev.

42. The method of claim 36 wherein the coexpressing is of: a first DNA construct which encodes the genome of the vector particles, a second DNA construct which encodes gag and pol proteins, and a third DNA construct which encodes the envelope protein.

43. The method of claim 37 wherein the coexpressing is of: a first DNA construct which encodes the genome of the vector particles, a second DNA construct which encodes gag and pol proteins, and a third DNA construct which encodes the envelope protein, wherein one of the DNA constructs optionally encodes a functionally active rev.

44. The method of claim 35 wherein the coexpressing includes expressing a DNA construct which encodes gag and pol proteins independent of auxiliary genes.

45. The method of claim 37 wherein the coexpressing includes expressing a DNA construct which encodes gag and pol proteins independent of auxiliary genes.

46. The method of claim 35 wherein rev is present or a functionally active rev is expressed.

47. The method of claim 37 wherein rev is present or a functionally active rev is expressed.

48. The method of claim 35 wherein the nucleic acid sequence(s) further includes one or more genes of interest.

49. The method of claim 36 wherein the nucleic acid sequence(s) further includes one or more genes of interest.

50. The method of claim 37 wherein the nucleic acid sequence(s) further consists essentially of one or more genes of interest.

51. The method of claim 35 wherein the genome further includes an operable promoter.

52. The method of claim 36 wherein the genome further includes an operable promoter.

53. The method of claim 37 wherein the genome further consists essentially of an operable promoter.

54. The method of claim 45 wherein the promoter is a non-retroviral promoter.

55. The method of claim 36 wherein the promoter is a non-retroviral promoter.

56. The method of claim 37 wherein the promoter is a non-retroviral promoter.

57. An infection and transduction competent, lentivirus-based, replication defective vector particle produced by the method of claim 35, wherein the particle lacks all functional lentiviral auxiliary gene products other than the optionally present functionally active rev.

58. An infection and transduction competent, lentivirus-based, replication defective vector particle produced by the method of claim 36, wherein the particle lacks all functional lentiviral auxiliary gene products other than the optionally present functionally active rev.

59. An infection and transduction competent, lentivirus-based, replication defective vector particle produced by the method of claim 37, wherein the particle lacks all functional lentiviral auxiliary gene products other than the optionally present functionally active rev.

60. An infection and transduction competent, lentivirus-based, replication defective vector particle produced by the method of claim 38, wherein the particle lacks all functional lentiviral auxiliary gene products other than the optionally present functionally active rev.

61. An infection and transduction competent, lentivirus-based, replication defective vector particle produced by the method of claim 39, wherein the particle lacks all functional lentiviral auxiliary gene products other than the optionally present functionally active rev.

62. An infection and transduction competent, lentivirus-based, replication defective vector particle produced by the method of claim 40, wherein the particle lacks all functional lentiviral auxiliary gene products other than the optionally present functionally active rev.

63. An isolated nucleic acid sequence encoding the components of the infection and transduction competent, lentivirus-based, replication defective vector particle as claimed in claim 1 or 2, comprising DNA construct(s) which encode the genome of the vector particle, gag and pol proteins, and an envelope protein, wherein, the nucleic acid sequence produces the lentivirus-based, replication defective vector particle, and, wherein: the DNA construct(s) optionally encode a functionally active rev; and all other functional auxiliary gene products are absent from the retroviral vector particle and producer cells in which the nucleic acid sequence is expressed, and are also absent from or disrupted in the nucleic acid sequence.

64. Isolated nucleic acid sequence(s) encoding the components of the infection and transduction competent, lentivirus-based, replication defective vector particle as claimed in claim 1 or 2, comprising construct(s) which encode the genome of the vector particle, gag and pot proteins, and an envelope protein, wherein all functional auxiliary gene products, or all functional auxiliary gene products except functionally active rev, are absent from the retroviral vector particle and producer cells in which the nucleic acid sequence(s) is/are expressed and are absent from or disrupted in the sequence(s).

65. Isolated nucleic acid sequence(s) encoding the components of the infection and transduction competent, lentivirus-based vector particle of claim 1 or 2, consisting essentially of construct(s) which encode(s) the RNA genome of the vector particle, gag and pol proteins, and an envelope protein, wherein the construct(s) optionally encode(s) functionally active rev.

66. The retroviral vector production system wherein according to claim 10 or 11 wherein the retroviral vector particle is based on HIV-1 and auxiliary genes vpu, vpr, vif, tat and nef are absent or are disrupted.

67. The retroviral particle of claim 1 or 2 which is based on HIV-1 and auxiliary genes vpu, vpr, vif, tat and nef are absent or are disrupted.

68. The retroviral particle of claim 1 or 2 which is based on HIV-1 and auxiliary genes vpu, vpr, vif, tat, rev and nef are absent or are disrupted.

69. A retroviral particle according to claim 1 or 2 wherein the envelope protein is VSV-G.

70. The retroviral vector production system wherein according to claim 10 or 11 wherein the functionally active rev is present as a constitutive transport element (CTE).

71. The retroviral particle of claim 1 or 2 wherein the functionally active rev is present as a constitutive transport element (CTE).

* * * * *

UNITED STATES PATENT AND TRADEMARK OFFICE
CERTIFICATE OF CORRECTION

PATENT NO. : 6,312,682 B1
DATED : November 6, 2001
INVENTOR(S) : Kingsman et al.

It is certified that error appears in the above-identified patent and that said Letters Patent is hereby corrected as shown below:

Column 12,
Lines 64-65, please change "producing infection" to -- producing the infection --.

Column 13,
Line 55, please change "lentivirus-basedvector" to -- lentivirus-based vector --.

Column 16,
Line 18, please change "gag and pot" to -- gag and pol --.
Line 32, please change "production system wherein" to -- production system --.

Signed and Sealed this

Seventeenth Day of December, 2002

JAMES E. ROGAN
*Director of the United States Patent and Trademark Office*